(12) United States Patent
Iida et al.

(10) Patent No.: US 6,320,331 B1
(45) Date of Patent: Nov. 20, 2001

(54) LIGHT SOURCE APPARATUS USING ELECTRIC LAMP AS LIGHT SOURCE

(75) Inventors: Mitsuru Iida, Saitama; Haruhiko Hibi, Tokyo, both of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/457,735

(22) Filed: Dec. 10, 1999

(30) Foreign Application Priority Data

Dec. 11, 1998 (JP) .................................................. 10-352617

(51) Int. Cl.$^7$ ........................................................ G05F 1/00
(52) U.S. Cl. ........................... 315/293; 315/291; 315/129; 315/363; 600/180; 600/178
(58) Field of Search ..................................... 315/293, 291, 315/297, 307, 224, 129, 131, 132, 363; 600/180, 178

(56) References Cited

U.S. PATENT DOCUMENTS

| | | | |
|---|---|---|---|
| 4,491,865 | * | 1/1985 | Danna et al. ............................ 358/98 |
| 4,532,918 | * | 8/1985 | Wheeler .................................... 128/6 |
| 4,646,721 | * | 3/1987 | Arakawa ................................... 128/6 |
| 5,091,678 | * | 2/1992 | Chin-Song ............................. 315/362 |
| 5,663,613 | * | 9/1997 | Yamashita et al. ................... 315/308 |
| 5,876,327 | * | 3/1999 | Tsuyuki et al. ....................... 600/112 |
| 6,034,487 | * | 3/2000 | Yamashita et al. ................... 315/244 |
| 6,043,609 | * | 3/2000 | George et al. ...................... 315/169.3 |
| 6,046,551 | * | 4/2000 | Kita ...................................... 315/307 |
| 6,051,939 | * | 4/2000 | Eckert ................................... 315/307 |

* cited by examiner

Primary Examiner—Don Wong
Assistant Examiner—Tuyet T. Vo
(74) Attorney, Agent, or Firm—Greenblum & Bernstein P.L.C.

(57) ABSTRACT

A light source apparatus is used in a video endoscope system having a charge coupled device (CCD) image sensor and a monitor. The light source apparatus provides illumination to a scene to be imaged by the CCD image sensor and displayed on the monitor. The light source apparatus includes a discharge lamp serving as a light source. The lamp is subject to progressive degradation during use so that its output light intensity achievable with a given level of input current gradually decreases through its lifetime. The current supplied to the lamp is controlled using a feedback control technique so as to maintain the output light intensity of the lamp at a substantially fixed, desired intensity level. In order to allow the operator to timely replace the discharge lamp with a new one, the input current to the discharge lamp is detected and compared to a threshold level. The threshold level may be selected to a level corresponding to the rated power of the lamp designated by the manufacturer. The input current has a tendency that its level for achieving a given level of output light intensity of the lamp gradually increases through the lifetime of the lamp, which is caused by progressive degradation of the lamp while the output light intensity level is controlled to be at a substantially fixed level. When the level of the input voltage has reached the threshold level, a visual alarm indication is provided on the monitor, indicating the necessity for replacement of the discharge lamp.

18 Claims, 5 Drawing Sheets

FIG. 5

LIGHT SOURCE APPARATUS USING ELECTRIC LAMP AS LIGHT SOURCE

The present disclosure relates to subject matter contained in Japanese Patent Application No. Hei-10-352617 filed on Dec. 11, 1998, which is expressly incorporated herein by reference in its entirety.

BACKGROUND OF THE INVENTION

1. Field of the Invention

The present invention relates to a light source apparatus using an electric lamp of the type called discharge lamp as a light source, which apparatus may be advantageously used in various applications and, in particular, in an illumination system for a video endoscope system.

2. Description of the Related Art

Video endoscope systems include an image sensor, such as a charge coupled device (CCD), for obtaining a scene image to be displayed on a screen of a monitor for viewing by the operator. An illumination system is required to provide an acceptable level of illumination to the scene for maintaining image quality of the scene. A typical illumination system for a video endoscope system includes a discharge lamp serving as a light source to generate light for illumination. It is desirable that a video endoscope has a light source which is capable of generating output light with high stability in its intensity. The stability in the output light intensity has two different aspects. One is that the light source should produce only small fluctuations in its output light intensity during a continuous operation, which may typically last for several hours. The other is that the light source should produce as small a decrease as possible in its output light intensity through its lifetime, which may typically last hundreds or thousands hours or more. However, gradual decrease in the output light intensity inevitably results from corresponding decrease in conversion efficiency from input electric power to output light energy of the lamp, which occurs due to several factors including progressive degradation of the electrodes of the discharge lamp. The gradual decrease in the output light intensity will mount up to a considerable fall in brightness of the discharge lamp after longtime use.

As apparent to those skilled in the art, the output light intensity level of a discharge lamp could be stabilized with ease by effecting any suitable feedback control technique to the lamp; however, a new problem would arise from this solution. Without any such control, progressive degradation of a discharge lamp will result in a considerable fall in brightness of the lamp, which can be utilized in fact as a convenient indication of the necessity for replacement of the lamp with a new one. Such indication is of particular importance for a discharge lamp used as a light source in a video endoscope system because a sudden failure of the lamp during operation of the video endoscope system is highly undesirable. Therefore, it is required that a discharge lamp used as a light source in a video endoscope system may be replaced before it terminates its life with a sudden failure, while at the same time any premature lamp replacement may be avoided for economical reasons. The latter requirement means that an appropriate indication of the necessity for lamp replacement is desired; however, the convenient indication that could be otherwise provided by a considerable fall in brightness of the lamp will be lost if feedback control is effected to the lamp in order to stabilize the output light intensity of the lamp.

Accordingly, there has been a long desire for a light source apparatus including a discharge lamp, wherein the apparatus may generate output light having high stability in its intensity, while at the same time the apparatus may provide an appropriate indication of the necessity for lamp replacement so that both a sudden failure of the discharge lamp during use of the apparatus and a premature replacement of the discharge lamp may be effectively avoided.

SUMMARY OF THE INVENTION

In view of the foregoing, it is an object of the present invention to provide a light source apparatus including a discharge lamp, the discharge lamp being subject to progressive degradation during use so that its output light intensity achievable with a given level of electrical input gradually decreases through its lifetime, wherein the output light intensity of the discharge lamp may be highly stabilized and maintained at a substantially fixed, desired intensity level, while at the same time the apparatus may provide an appropriate indication of the necessity for replacement of discharge lamp so as to effectively avoid both a sudden failure of the discharge lamp during use of the apparatus and a premature replacement of the discharge lamp.

In accordance with one aspect of the present invention, there is provided a light source apparatus including a discharge lamp, the discharge lamp being subject to progressive degradation during use so that its output light intensity achievable with a given level of electrical input gradually decreases through its lifetime, the apparatus comprising: an output light intensity control for controlling electrical input to the discharge lamp in order to maintain output light intensity of the discharge lamp at a substantially fixed, desired intensity level; a detector for detecting an electrical parameter relating to electrical input to the discharge lamp, the electrical parameter having a tendency that its level for achieving a given level of output light intensity of the discharge lamp gradually and monotonically varies through lifetime of the discharge lamp; and an indicator for determining when level of the electrical parameter detected by the detector has reached a threshold level and providing an indication when it determines so.

The electrical parameter may be input current supplied to the discharge lamp, which has a tendency that its level for achieving a given level of output light intensity of the discharge lamp gradually increases through lifetime of the discharge lamp. In such case, the indicator may determine when level of the input current has increased to reach a threshold current level and provide an indication when it determines so. Also, in such case, the discharge lamp may have a lower-limit input-current level such that the discharge lamp is incapable of stable operation unless it is supplied with input current at a level higher than the lower-limit input-current level; and the desired intensity level of output light of the discharge lamp may be selected such that the discharge lamp will produce output light at the desired intensity level when it is supplied with input current at a level substantially equal to and slightly higher than the lower-limit input-current. Further, the discharge lamp may have a rated power designated by a manufacturer thereof; and the threshold current level may be selected to be substantially equal to such a level of input current to the discharge lamp that will occur when the discharge lamp is supplied with the rated power.

Alternatively, the electrical parameter may be input power supplied to the discharge lamp, which has a tendency that its level for achieving a given level of output light intensity of the discharge lamp gradually increases through lifetime of the discharge lamp. In such case, the indicator may determine when level of the input power has increased to reach a threshold power level and provide an indication when it determines so.

Still alternatively, the electrical parameter may be input voltage applied across the discharge lamp, which has a tendency that its level for achieving a given level of output light intensity of the discharge lamp gradually increases through lifetime of the discharge lamp. In such case, the indicator may determine when level of the input voltage has increased to reach a threshold voltage level and provide an indication when it determines so.

The detector may provide a detection signal indicative of a detected level of the electrical parameter. The indicator may comprise: a threshold signal generator for generating a threshold signal indicative of the threshold level; a comparator connected to receive the detection signal and the threshold signal so as to produce an output signal indicative of comparison between the detection signal and the threshold signal; and an alarm generator for responding to the output signal from the comparator by selectively generating an alarm indication. In such case, the alarm indication may comprise an indication indicating necessity for replacement of discharge lamp. Also, the apparatus may further comprise a monitor having a display screen, while the alarm indication may comprise a visual alarm indication displayed on the screen of the monitor.

The output light intensity control may comprise: an output light intensity detector for detecting output light intensity of the discharge lamp and providing an intensity detection signal indicative of a detected level of output light intensity of the discharge lamp; a reference signal generator for generating a reference signal indicative of a reference level corresponding to the desired intensity level of output light of the discharge lamp; a differential generator connected to receive the intensity detection signal and the reference signal so as to produce an output signal indicative of difference in level between the detection signal and the reference signal; a control signal generator for responding the output signal from the differential generator by generating a control signal; and a current control element for controlling input current to the discharge lamp in response to the control signal.

The apparatus may be advantageously incorporated in a video endoscope system including an endoscope having a viewing head and a solid-state image sensor housed in the viewing head. In such case, the apparatus may provide illumination to a scene to be imaged by the solid-state image sensor. Further, the video endoscope system may include a monitor having a screen for displaying thereon a scene imaged by the solid-state image sensor and the indicator may provide a visual alarm indication displayed on the screen of the monitor, indicating necessity for replacement of discharge lamp.

In accordance with another aspect of the present invention, there is provided a light source apparatus for a video endoscope system including an endoscope with an image sensor for sensing an image under illumination provided by the light source apparatus, the light source apparatus comprising: a discharge lamp; a power supply for the discharge lamp; an output light intensity detector for detecting intensity level of output light of the discharge lamp to be supplied to the endoscope; an electrical input control for controlling electrical input to the discharge lamp in order to maintain output light intensity of the discharge lamp as detected by the output light intensity detector at a substantially fixed, desired intensity level; and the desired intensity level being selected such that the discharge lamp will produce output light at the desired intensity level when it is supplied with electrical input at a level below a rated electrical input level of the discharge lamp.

The electrical input control may comprise input current control for controlling input current to the discharge lamp. In such case, the discharge lamp may have a lower-limit input-current level such that the discharge lamp is incapable of stable operation unless it is supplied with input current at a level higher than the lower-limit input-current level, and the desired intensity level of output light of the discharge lamp may be selected such that the discharge lamp will produce output light at the desired intensity level when it is supplied with input current at a level substantially equal to and slightly higher than the lower-limit input-current.

The light source apparatus may further comprise: an electrical input detector for detecting electrical input to the discharge lamp; and an indicator for determining when level of electrical input to the lamp as detected by the electrical input detector has reached a threshold level and providing an indication when it determines so. The threshold level may be selected to be substantially equal to the rated electrical input level of the discharge lamp. Further, the electrical input detector may provide a detection signal indicative of a detected level of electrical input to the discharge lamp, and the indicator may comprise: a threshold signal generator for generating a threshold signal indicative of the threshold level; a comparator connected to receive the detection signal and the threshold signal so as to produce an output signal indicative of comparison between the detection signal and the threshold signal; and an alarm generator for responding to the output signal from the comparator by selectively generating an alarm indication. The alarm indication may comprise an indication indicating necessity for replacement of discharge lamp.

BRIEF DESCRIPTION OF THE DRAWINGS

The above and other objects, features and advantages of the present invention will be apparent from the following detailed description of a preferred embodiment thereof, reference being made to the accompanying drawings, in which.

DETAILED DESCRIPTION OF A PREFERRED EMBODIMENT

Figure 1:
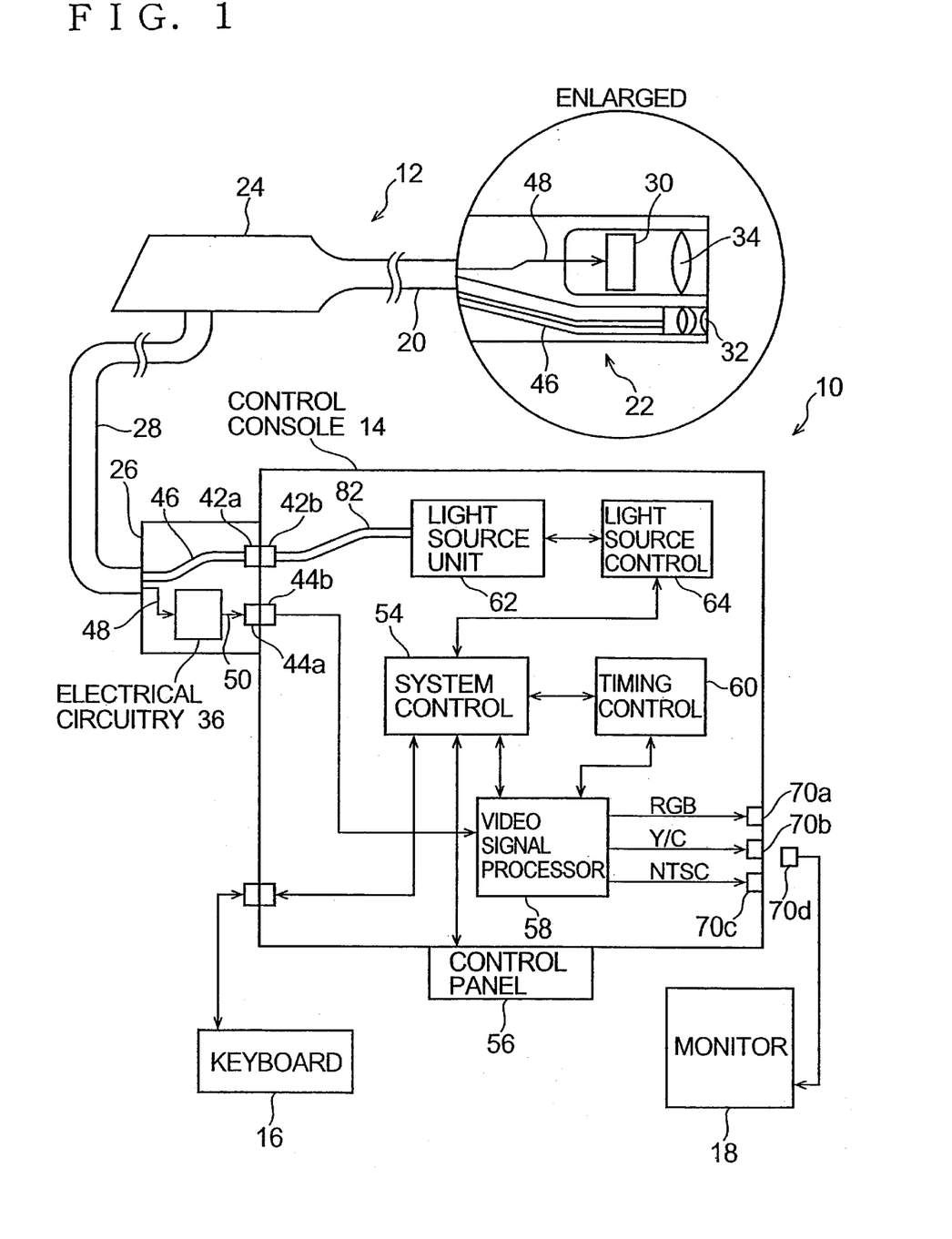
FIG. 1 is a highly simplified diagram showing a color video endoscope system including a light source apparatus constructed and arranged in accordance with a preferred embodiment of the present invention.

Now with reference to the accompanying drawings, a preferred embodiment of the present invention will be described in detail. Referring first to FIG. 1, there is shown a color video endoscope system 10 in which a light source apparatus constructed and arranged in accordance with a preferred embodiment of the present invention is incorporated. In general, the color video endoscope system 10 includes an endoscope 12, a control console 14, a keyboard 16 and a monitor 18. The control console 14 receives video signals from the endoscope 12 and provides the processed video signals to the monitor 18 for display of the image viewed through the endoscope 12.

The endoscope 12 includes a flexible insertion tube 20 having a viewing head 22 at its distal end (shown enlarged in FIG. 1), an operating section 24 for control of the endoscope 12 by the operator, a connector block 26 for mechanical, electrical and optical connections of the endoscope 12 to the control console 14, and a flexible connector cable 28 interconnecting the operating section 24 and the connector block 26. In operation, the insertion tube 20 of the endoscope 12 is inserted into a cavity in the body of a patient, as is well known in the art.

Contained in the viewing head 22 of the endoscope 12 are: a solid-state image sensor comprising a charge coupled device (CCD) 30; an illumination lens system 32 for illuminating a scene to be imaged by the CCD 30; and an objective lens system 34 for directing and focusing the reflected light from the scene back to the CCD 30. Although simple lens systems are depicted in the drawing, it should be clear to those skilled in the art that more complex lens systems may be typically used in place of them. The endoscope 12 also includes electrical circuitry 36 disposed within the connector block 26. The electrical circuitry 36 is associated with the CCD 30 and serves to trigger the CCD 30 to transfer its output data signal as well as serves to amplify the output data signal from the CCD 30 to a suitable level to be feed to the control console 14.

The CCD 30 is a conventional color charge coupled device of the type commonly used in compact image sensing apparatus. The CCD 30 comprises three photodiode arrays corresponding to the three primary colors of light, red, green and blue colors, with associated optical filters. The photodiode arrays are formed on a single substrate, so that the CCD 30 has a single, united structure. The photodiode arrays produce three separate, color signals corresponding to red, green and blue colors, respectively, which are representative of the color components of the scene image.

The present invention is not limited to the use of a color charge coupled device of the type described above; in fact, various other types of charge coupled devices may be used in place of the CCD 30. For example, a charge coupled device comprising a single photodiode array may be used. In such case, suitable means for generating sequential fields of colored light of red, green and blue may be provided in the light source apparatus. One well known example of such means is a color filter wheel having red, green and blue filters rotated in synchronism with the operation of the charge coupled device.

The connector block 26 has an optical connector 42a and an electrical connector 44a mounted therein. The control console 14 has an optical connector 42b and an electrical connector 44b for mating with the connectors 42a and 44a, respectively, in the connector block 26. When the connector block 26 is plugged into the control console 14, the connector pairs 42a, 42b and 44a, 44b provide optical and electrical connections, respectively, between the endoscope 12 and the control console 14.

The endoscope 12 includes a fiber optic light guide 46 having a distal end facing to the illumination lens system 32 in the viewing head 22 and a proximal end connected to the optical connector 42a in the connector block 26. Light is supplied from the light source apparatus in the control console 14 through the mating optical connectors 42a and 42b and the fiber optic light guide 46 to the viewing head 22 of the endoscope 12, so as to provide illumination to a scene to be imaged by the CCD 30. With this arrangement, the CCD 30 senses an image of the scene under illumination provided by the light source apparatus of the present invention.

The connector block 26 is further provided with first and second electrical connector cables 48 and 50. The first cable 48 interconnects the CCD 30 in the viewing head 22 and the electrical circuitry 36 in the connector block 26. The second cable 50 interconnects the electrical circuitry 36 and the electrical connector 44a.

The endoscope 12 also includes many other elements including a conduit for water supply, a conduit for air supply, a drainage conduit, valves for the conduits, wires for the valves, and a biopsy channel through which a pair of biopsy forceps may be inserted. Such elements are, however, not directly related to the present invention and thus not shown nor described in detail for simplicity. FIG. 1 shows only those of the elements and components of the video endoscope system 10 which are directly related to and thus of significance to the present invention.

The control console 14 includes a system control 54, a control panel 56, a video signal processor 58, a timing control 60, a light source unit 62 (shown in more detail in FIG. 2) and a light source control 64 (shown in more detail in FIG. 3), all of which are housed within a console housing (not shown) except the control panel 56, which is mounted on the outside of the console housing to be accessible to the operator.

The system control 54 is a microcomputer-based control unit so programmed as to control various operations and functions of the video endoscope system 10. Specifically, the system control 54 controls the video signal processor 58 and the timing control 60 in order to generate video signals for display of the scene image together with various indications on the screen of the monitor 18. Further, the system control 54 controls the light source unit 62 through the light source control 64 as described in greater detail below with reference to FIGS. 2 through 5.

As seen from FIG. 1, the system control 54 is connected also to the keyboard 16 and the control panel 56. The control panel 56 comprises a conventional user interface device often called a "touch-sensitive display." The touch-sensitive display includes a liquid crystal display (LCD) and a transparent touch panel superposed on the screen of the LCD. Various software-implemented keys may be displayed on the LCD, and the touch panel is capable of detecting the position of the operator's finger touching such a part of the surface of the touch panel that is just on a particular key. The operator may control and/or select operations and functions of the endoscope system 10 through the control panel 56. The keyboard 16 is used by the operator to enter control parameters and text data into the system control 54.

The video signal processor 58 receives three color signals from the electrical circuitry 36 of the endoscope 12 and effects necessary corrections to the signals. Further, the video signal processor 58 and the timing control 60 cooperate to process the corrected color signals to generate three forms of video signals, including RGB signals (a set of red, green and blue signals), Y/C signals (a combination of luminance and chrominance signals) and a NTSC composite signal (a modulated signal compatible with ordinary television sets). How to generate each of these video signals is well known in the art and therefore is not described herein for simplicity. The three forms of video signals are output to electrical connectors 70*a*, 70*b* and 70*c*, respectively. Among the connectors 70*a*, 70*b* and 70*c*, the connector that provides video signals compatible with the monitor 18 to be used is selected for connection with the monitor 18 through an electrical connector 70*d* adapted for that form of video signals. The timing control 60 also includes video memories and serves to control vertical and horizontal positions of the scene image displayed on the screen of the monitor 18.

The control console 14 also includes many other elements including a water pump, an air pump, valve controls and various indicators, which are, however, not directly related to the present invention and thus not shown nor described in detail for simplicity.

Figure 2:
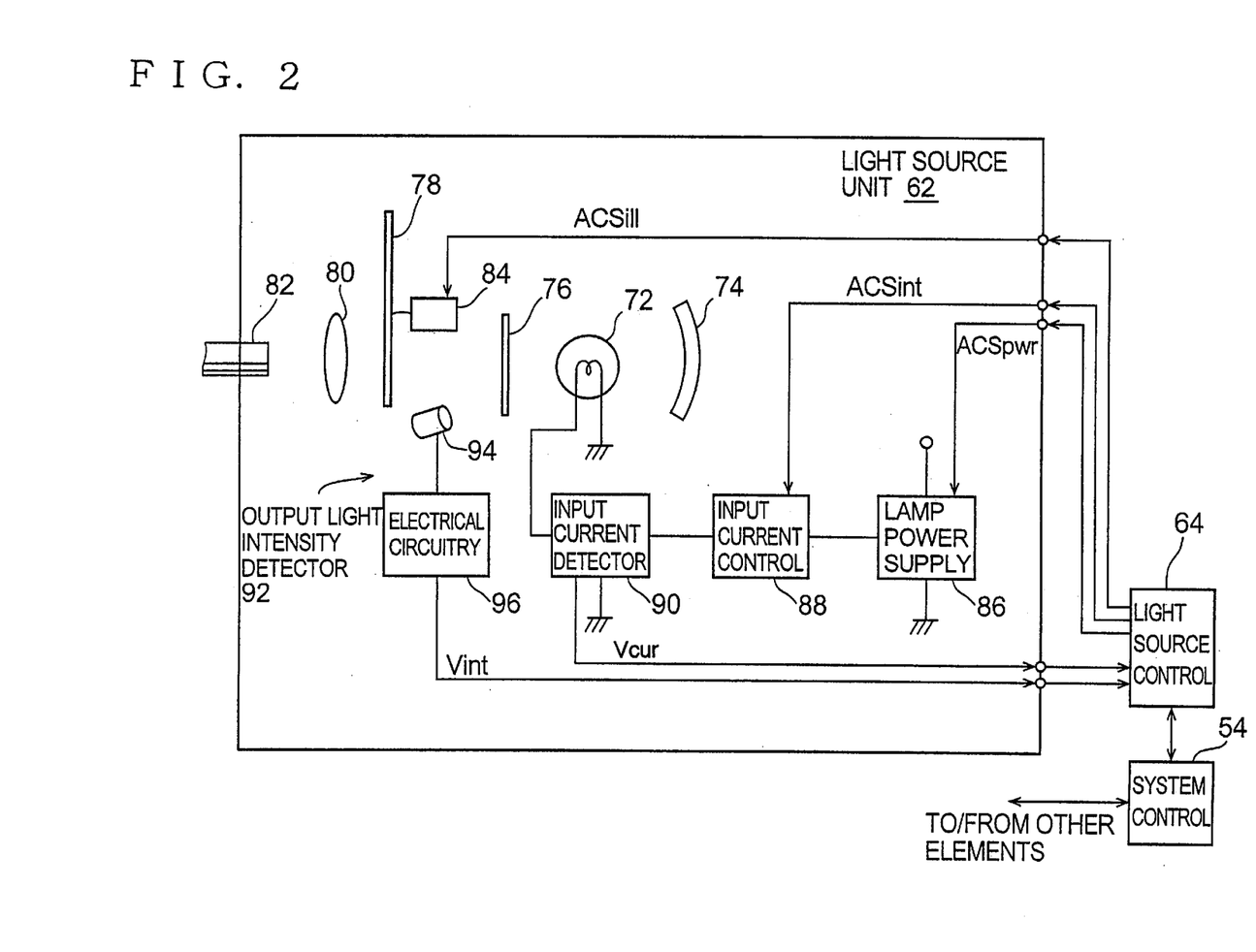
FIG. 2 is a simplified diagram showing a light source unit in FIG. 1 in more detail.

Referring next to FIG. 2, the light source unit 62 will be described in more detail. The light source unit 62 includes an electric lamp 72 serving as a light source. The electric lamp 72 comprises a discharge lamp, such as a xenon short-arc lamp or any other suitable high intensity discharge lamp. As may be common to most of the discharge lamps usable as a light source, the discharge lamp 72 is subject to progressive degradation during use so that its output light intensity achievable with a given level of electrical input gradually decreases through its lifetime. The gradual decrease in the output light intensity results from corresponding decrease in conversion efficiency from input electric power to output light energy of the lamp, which occurs due to several factors including progressive degradation of the electrodes of the discharge lamp.

As described above, a substantial decrease in the output light intensity (or brightness) of a discharge lamp occurring after longtime use may have been utilized as a convenient indication of the necessity for replacement of the lamp with a new one; however, such a substantial decrease in brightness of a discharge lamp may often cause inconveniences, in particular when the lamp is used as a light source in a video endoscope system. In contrast, according to the present invention, the output light intensity of the discharge lamp 72 may be maintained at a substantially fixed, desired intensity level, while at the same time any necessity for replacement of the discharge lamp 72 may be appropriately determined and indicated to the operator, as clearly shown in the following description.

The light source unit 62 further includes a reflector 74, an infrared filter 76, a mechanical light adjuster 78, a lens 80 and a fiber optic light guide 82, each of which may be found in typical, conventional light source units. The mechanical light adjuster 78 is capable of controlling the amount of light passing through it, and the amount of light passed therethrough is focused by the lens 80 upon the light entrance face of the fiber optic light guide 82 and guided thereby to the optical connector 42*b* (FIG. 1). The mechanical light adjuster 78 may comprise, for example, a neutral density filter wheel well known in the art. Such wheel has varying density for allowing different amounts of light to pass through the wheel depending on the angular position of the wheel. The mechanical light adjuster 78 is provided with an actuator 84 which is controlled by an illumination control signal $ACS_{ill}$ provided from the light source control 64 for controlling the illuminance in the scene to be imaged by the CCD image sensor 30. Two different modes are provided for such illuminance control operation and selectable by the operator. In one mode, called manual mode, the operator sets the mechanical light adjuster 78 to a desired position by operating an appropriate software-implemented key on the control panel 56. In the other mode, called automatic mode, the mechanical light adjuster 78 is controlled by the system control 54 to maintain illuminance in the scene of view field at a desired level, which illuminance level could otherwise vary due to changes in distance between the viewing head 22 and the viewed objects in the scene. In the automatic mode, an illuminance sensor (not shown) is used to sense illuminance in the scene of view field so as to generate an illuminance signal, which is then used by the system control 54 to effect automatic illuminance control.

The light source unit 62 further includes: a lamp power supply 86; an input current control 88 connected to control input current supplied to the lamp 72; an input current detector 90 connected to detect input current to the lamp 72 and providing a current detection signal $V_{cur}$, which is a voltage signal indicative of the detected current level; and an output light intensity detector 92 so disposed as to detect the intensity level of the output light generated by the discharge lamp 72 and supplied to the endoscope 12, and providing an intensity detection signal $V_{int}$, which is a voltage signal indicative of the detected intensity level.

More particularly, the input current control 88 may comprise a suitable current control element, such as a thyristor or the like, with associated electrical circuitry required for appropriate operation of the current control element. It is also contemplated that any other type of electrical input control for controlling electrical input to the discharge lamp 72 may be used in place of the input current control 88, such as an input voltage control or an input power control.

The input current detector 90 may comprise any of various known arrangements of electrical circuitry suitable for the purpose. The output light intensity detector 92 may comprise a photo transistor 94 and electrical circuitry 96 associated with the photo transistor 94. The electrical circuitry 96 generates the intensity detection signal $V_{int}$ as a voltage signal having its voltage level corresponding to current flowing through the photo transistor 94 and thus indicative of the intensity level of the light beam emitting from the lamp 72 and incident upon the sensitive surface of the photo transistor 94. The detection signals $V_{cur}$ and $V_{int}$ thus generated in the light source unit 62 are supplied to the light source control 64, while the light source control 64 supplies to the light source unit 62 three control signals as described below with reference to FIG. 3.

Figure 3:
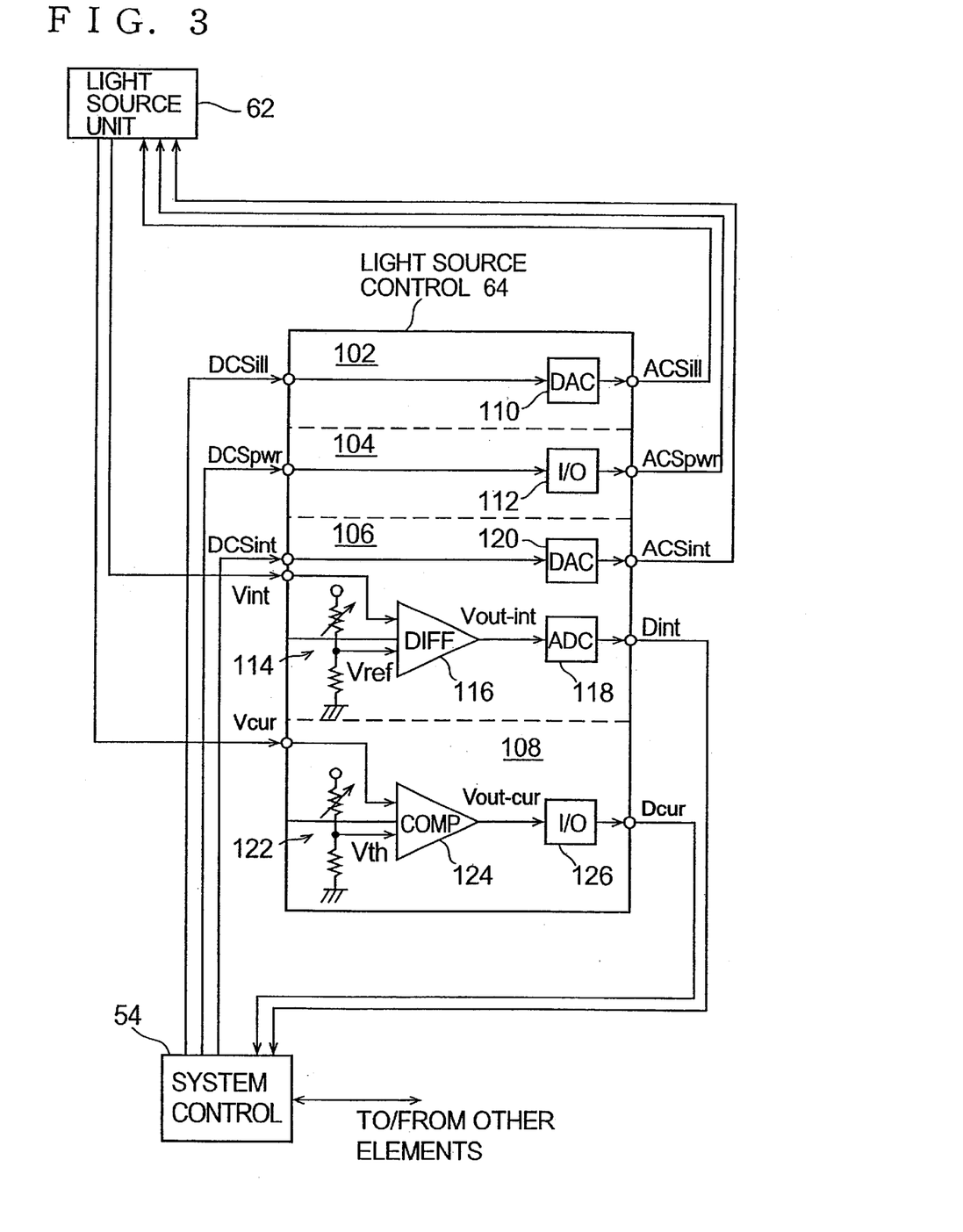
FIG. 3 is a simplified diagram showing a light source control in FIG. 1 in more detail.

Referring to FIG. 3, the light source control 64 will be described in more detail. The light source control 64 includes an illuminance control section 102, a lamp power supply on/off section 104, an output light intensity level control section 106 and a comparison section 108.

The illuminance control section 102 includes an digital-to-analog converter (DAC) 110. The DAC 110 is connected to receive from the system control 54 a digital control signal $DSC_{ill}$ and converts it into a corresponding analog control signal $ACS_{ill}$, which is a voltage signal for controlling the actuator 84 to set the mechanical light adjuster 78 to a desired position. When an illuminance control operation is performed, either in the manual or automatic mode of operation as described above, the system control 54 generates the digital control signal $DSC_{ill}$ having an appropriate value and supplies it to the light source control 64.

The lamp power supply on/off section 104 includes an interface (I/O) 112, which is connected to receive from the system control 54 a binary digital control signal $DCS_{pwr}$ indicative of whether the lamp power supply 86 should be on or off. The I/O 112 converts the control signal $DCS_{pwr}$ into a corresponding drive signal $ACS_{pwr}$ and supplies it to the light source control 64 in order to turn on/off the lamp power supply 86 provided in the light source unit 62.

The output light intensity level control section 106 includes an adjustable voltage divider 114, a differential amplifier (DIFF) 116, an analog-to-digital converter (ADC) 118 and a digital-to-analog converter (DAC) 120. The adjustable voltage divider 114 serves as a reference signal generator for generating a reference signal $V_{ref}$, which is a voltage signal indicative of a reference level corresponding to a desired intensity level of the output light of the lamp 72. We describe later how to select the "desired intensity level" in detail. The differential amplifier 116 has two inputs connected to receive the intensity detection signal $V_{int}$ and the reference signal $V_{ref}$ so as to generate an output signal $V_{out-int}$ which is an analog voltage signal indicative of the difference in level between the intensity detection signal $V_{int}$ and the reference signal $V_{ref}$. The output signal $V_{out-int}$ is then converted into a corresponding digital signal $D_{int}$ by the ADC 118 and read into the system control 54. Specifically, the digital signal $D_{int}$, has a zero value if the intensity detection signal $V_{int}$ and the reference signal $V_{ref}$ are at the same level, a negative value if the former has a lower level than the latter, and a positive value if the former has a higher level than the latter. The value of the signal $D_{int}$ varies proportional to the difference in level between the signals $V_{int}$ and $V_{ref}$. The system control 54 uses the signal $D_{int}$ as a feedback signal so as to generates a digital control signal $DCS_{int}$, through procedure steps described later with reference to FIG. 5. The DAC 120 converts the digital control signal $DCS_{int}$ into a corresponding analog control signal $ACS_{int}$, which is used as a control signal for controlling the input current control 88 in the light source unit 62. With this arrangement, the system control 54, the light source unit 62 and the light source control 64 together constitute an output light intensity control facility for effecting feedback control to the electrical input (i.e., the input current) to the lamp 72 in order to maintain the output light intensity of the lamp 72 at a substantially fixed, desired intensity level.

As described above, the discharge lamp 72 is subject to progressive degradation during use so that its output light intensity achievable with a given level of input current gradually decreases through its lifetime. However, the output light intensity of the lamp 72 is actually maintained at a substantially fixed level by virtue of the feedback control thereto as described above, so that the input current supplied to the lamp 72 has a tendency that its level for achieving the desired intensity level of the output light of the lamp 72 gradually and monotonically increases through the lifetime of the discharge lamp 72. This monotonic (or one-way) variation in the level of the input voltage to the lamp 72 is utilized by the present invention for advantageously determining any necessity for replacement of the lamp 72 with a new one. Specifically, for this purpose, the comparison section 108 includes an adjustable voltage divider 122 and a comparator 124. The adjustable voltage divider 122 serves as a threshold signal generator for generating a threshold signal $V_{th}$, which is a voltage signal indicative of a threshold level for the input current to the lamp 72. The threshold level is utilized such that an indication of the necessity for lamp replacement is provided when the level of the input current to the lamp 72 has reached the threshold level. We describe later how to select the "threshold level" in detail. The comparator 124 has two inputs connected to receive the current detection signal $V_{cur}$ and the threshold signal $V_{th}$ so as to generate an output signal $V_{out-cur}$ which is a voltage signal indicative of the comparison between the two input signals by changing its level between high and low levels depending on the comparison. The output signal $V_{out-cur}$ is converted into a corresponding digital signal $D_{cur}$ by the I/O 126 and then read into the system control 54, which determines whether the signal $D_{cur}$ is at high level or low level, and responds to the signal $D_{cur}$ by selectively generating (i.e., generating only when the signal $D_{cur}$ shows that the level of the current detection signal $V_{cur}$ is equal to or higher than that of the threshold signal $V_{th}$) a visual alarm indication on the screen of the monitor 18, indicating the necessity for replacement of discharge lamp. In order to generate the visual alarm indication, the system control 54 provokes an alarm indication activation routine to control the video signal processor 58 and the timing control 60. With this arrangement, the system control 54, the video signal processor 58, the timing control 60, the light source unit 62, the light source control 64 and the monitor 18 together constitute an indicator for determining when the level of the electrical parameter (i.e., the input current to the lamp 72) detected by the current detector 90 has reached the threshold level and providing an indication when it determines so. In particular, the system control 54, the video signal processor 58, the timing control 60 and the monitor 18 together constitute an alarm generator for responding to the output signal $V_{out-cur}$ from the comparator 124 by selectively generating a visual alarm indication, prompting the operator to replace the discharge lamp 72.

The selections of the "desired intensity level" of the output light of the lamp 72 and the "threshold level" of the input current to the lamp 72 are of significance to the present invention, and thus have to be selected to appropriate levels. It is known that any discharge lamp has a lower-limit input-current level such that the discharge lamp is incapable of stable operation unless it is supplied with input current at a level higher than the lower-limit input-current level. It is also known that almost every discharge lamp available in the market has a rated power designated by the manufacturer, with which the discharge lamp is capable of operation with a good performance and with an acceptable lifetime. Using the lower-limit input-current level and the rated power of a discharge lamp, the "desired intensity level" and the "threshold level" suitable for the lamp may be conveniently selected with ease.

Specifically, with the embodiment shown and described, the desired intensity level of the output light of the discharge lamp 72 is selected such that the lamp 72 will produce output light at the desired intensity level when it is supplied with input current at a level substantially equal to and slightly higher than the lower-limit input-current level. The lower-limit input-current level of the discharge lamp 72 is apparently lower than the current level that will occur when the lamp 72 is supplied with input power at the level of the rated power. Thus, this selection of the desired intensity level may be expressed in other words: the desired intensity level is selected such that the lamp 72 will produce output light at the desired intensity level when it is supplied with electrical power at a level below the rated power. In any case, by selecting the desired intensity level of the lamp 72 in this manner, the lamp 72 may have a relatively long, expected lifetime because the speed of degradation of a discharge lamp generally depends on the intensity level of the output light it generates.

Also in this embodiment, the threshold level of the input current to the lamp 72 is selected to be substantially equal to such a level of input current to the lamp 72 that will occur when the discharge lamp is supplied with the rated power. Here it is noted that the threshold level thus selected will be higher than the lower-limit input-current level. Therefore, as the result of the feedback control effected to the lamp 72 in order to compensate for inevitable decrease in its energy conversion efficiency caused by degradation of the lamp 72, the input current actually supplied to the lamp 72 will gradually and monotonically increase from the initial level (i.e., the level substantially equal to and slightly higher than the lower-limit input-current level) toward the threshold level, and when it has reached the threshold level, a visual alarm is produced to prompt the operator to replace the lamp 72. Because the rated power is typically near the upper limit of the acceptable input-power range for the discharge lamp to operate with a good performance, selection of the threshold level in the manner may provide advantageous results in view of the performance of the discharge lamp 72.

Figure 4:
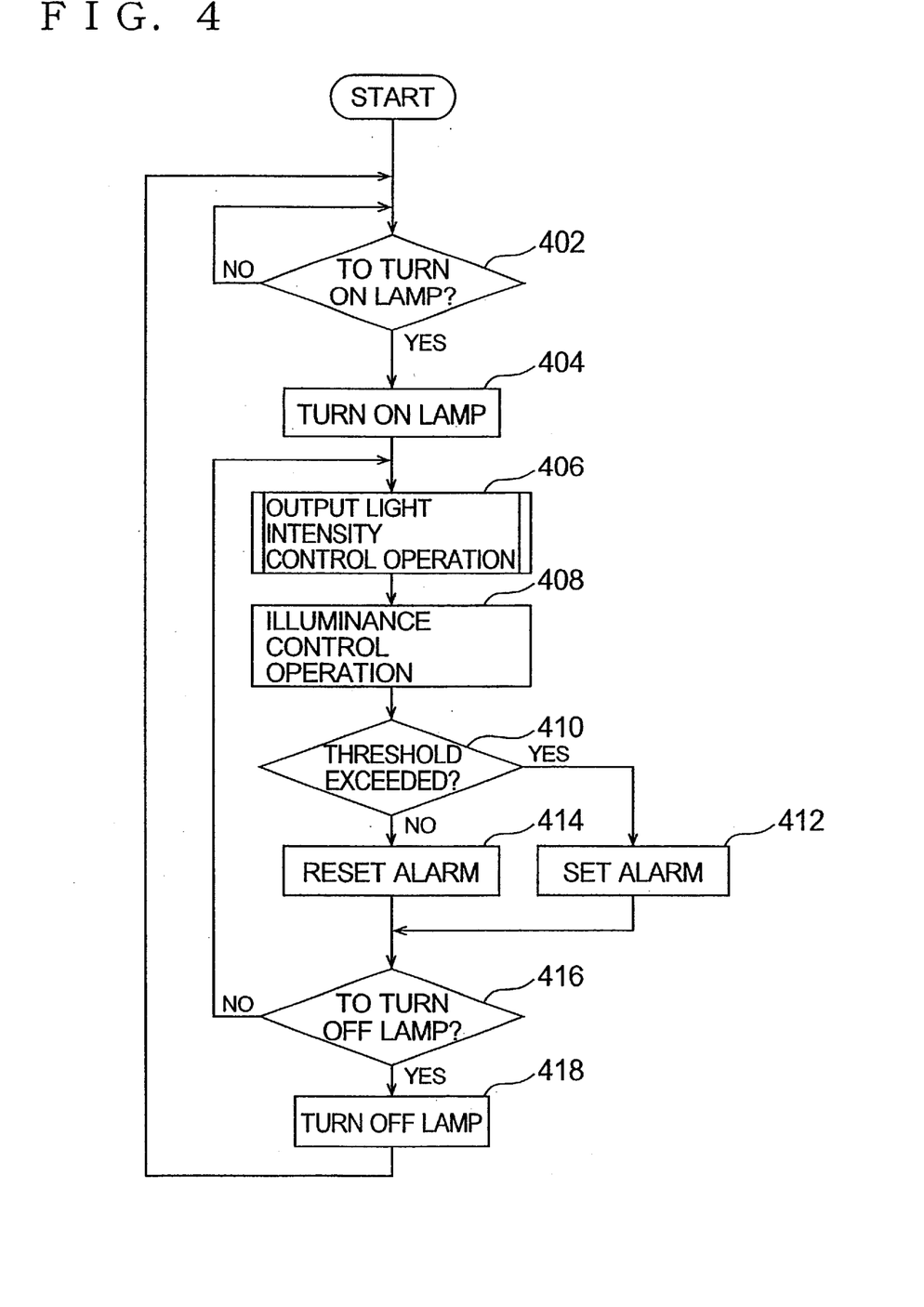
FIG. 4 is a flow diagram illustrating the process steps performed by a system control in FIG. 1 in connection with operations of the light source apparatus of FIG. 1.
Figure 5:
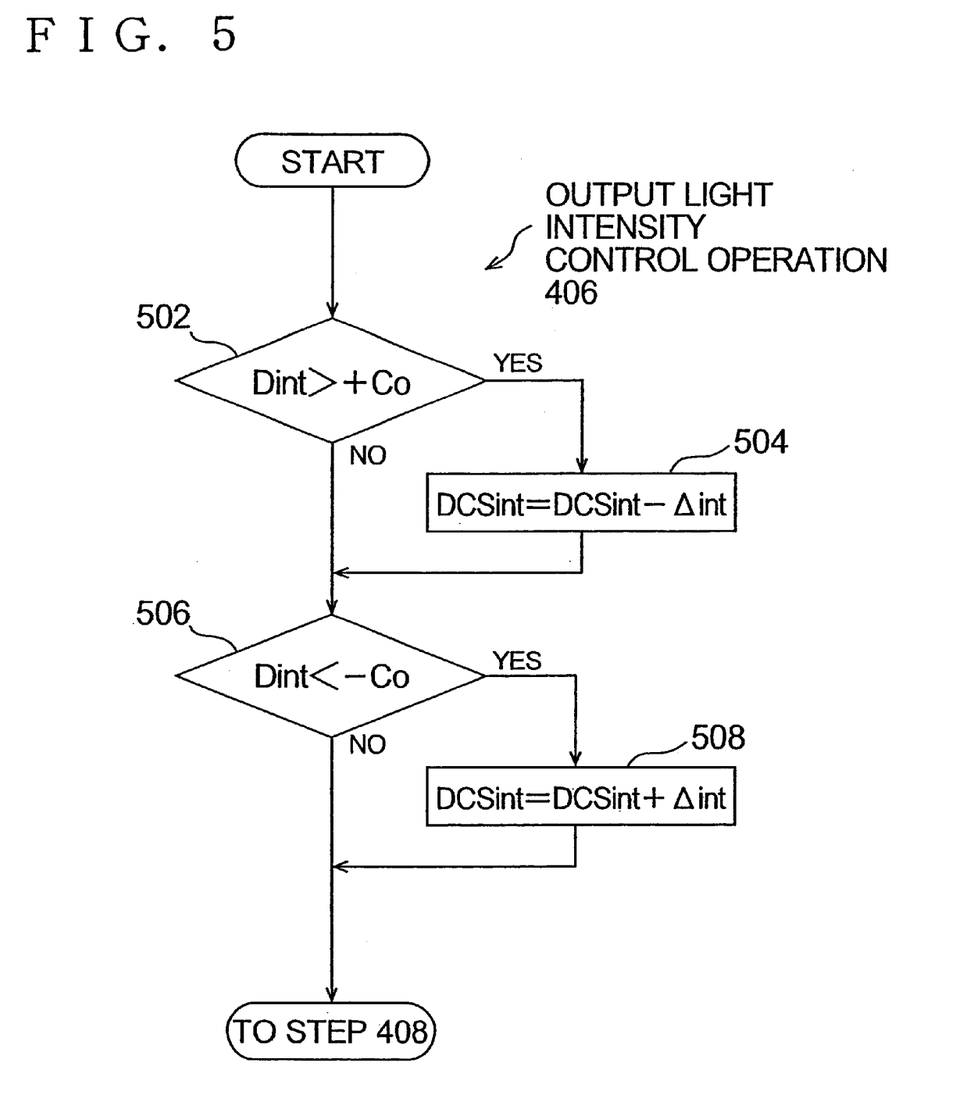
FIG. 5 is a flow diagram illustrating an output light intensity control operation in FIG. 4 in more detail.

Referring next to FIGS. 4 and 5, the process steps performed by the system control 54 in connection with the control operations of the light source apparatus are described.

In FIG. 4, at step 402, it is determined whether the operator has selected to turn on the lamp 72 by touching the control panel 56 with his/her finger. If so, the procedure proceeds to step 404, at which the system control 54 turns on the lamp 72 by activating the lamp power supply 86 through the lamp power supply on/off section 104 of the light source control 64. Otherwise, the procedure continues to loop within step 402. From step 404 the procedure proceeds to step 406, at which an output light intensity control operation is performed, which operation is described below in detail with reference to FIG. 5. Then, at step 408 an illuminance control operation is performed by actuating the mechanical light adjuster 78, as described above in connection with the illuminance control section 102 of the light source control 64.

Thereafter, at step 410 it is determined whether the level of input current to the lamp 72 has reached or exceeded the threshold level. If so, the procedure proceeds to step 412, at which a visual alarm indication is issued on the monitor 18 if such an indication is not yet provided, or maintained on the monitor 18 if already provided. Otherwise, the procedure proceeds to step 414, at which no issuance of a visual alarm indication is maintained, or an visual alarm indication is removed from the monitor 18 if already issued. In either case, the procedure then proceeds to step 416, at which it is determined whether the operator has selected to turn off the lamp 72. If so, the system control 54 turns off the lamp 72 at step 418 and the procedure loops back to step 402. Otherwise, the procedure loops back to step 406 from step 416.

FIG. 5 illustrates the output light intensity control operation shown at step 406 of FIG. 4 in some detail. This control operation may be possibly performed in various appropriate forms of procedures, and the method described below is merely an example selected from among them. For the method illustrated in FIG. 5, a dead band for the control operation is established for control stability. The dead band is defined as the range $-C_o$ to $+C_o$ of the value of the digital control signal $DCS_{int}$ (this signal is described previously in connection with the output light intensity level control section 106 of the light source control 64.) In addition, an increment $\Delta_{int}$ for incrementing/decrementing the value of the signal $DCS_{int}$ is predefined. The increment $\Delta_{int}$ is well smaller than twice the value $C_o$, i.e., the width of the dead band. At step 502, it is determined whether the signal $DCS_{int}$ has a value greater than $+C_o$. If so, the procedure proceeds to step 504, at which the signal $DCS_{int}$ is updated by decrementing its value by $\Delta_{int}$. Otherwise, step 504 is bypassed. Then, at step 506, it is determined whether the signal $DCS_{int}$ has a value smaller than $-C_o$. If so, the procedure proceeds to step 508, at which the signal $DCS_{int}$ is updated by incrementing its value by $\Delta_{int}$. Otherwise, step 506 is bypassed. Then, the control operation ends and the procedure proceeds to step 408 of FIG. 4. In this manner, the value of the digital control signal $DCS_{int}$ for controlling the input current to the lamp 72 is kept within the range $-C_o$ to $+C_o$, with the result that the output light intensity of the lamp 72 is maintained at a substantially fixed level, with which the intensity detection signal $V_{int}$ will be at substantially the same level as the reference signal $V_{th}$.

In the embodiment described above, the input current to the lamp 72 is selected as the electrical parameter that relates to the electrical input to the lamp 72 and that is detected for the purpose of controlling the output light intensity of the lamp 72. The electrical parameter which may be used for this purpose, however, is not limited to the input current to the lamp. The only requirement for such an electrical parameter is that it has a tendency that its level for achieving a given level of output light intensity of the discharge lamp gradually and monotonically varies through lifetime of the lamp. For example, with many of the discharge lamps usable as a light source, progressive degradation of the lamp inevitably results in corresponding decrease in conversion efficiency from input electric power to output light energy of the lamp, so that more electric input power is required for providing the same intensity level of output light after longtime use. This means that the input power to a discharge lamp has a tendency that its level for achieving a given intensity level of output light gradually increases through the lifetime of the lamp. Thus, the input power to the lamp may be alternatively used as the above-mentioned electrical parameter, with corresponding modifications to the light source unit 62 and the light source control 64 being effected in order to determine when the level of the input power has increased to reach a threshold power level and provide an indication when it determines so.

Still alternatively, for some discharge lamps, the input voltage applied across the lamp may have a tendency that its level for achieving a given intensity level of output light gradually increases through the lifetime of the lamp. In such case, the input voltage to the lamp may be used as the above-mentioned electrical parameter, with corresponding modifications to the light source unit 62 and the light source control 64 being effected in order to determine when the level of the input voltage has increased to reach a threshold voltage level and provide an indication when it determines so. Other electrical parameters, such as impedance of the lamp, may be possibly used for the purpose as well.

Having described the present invention with reference to the preferred embodiment thereof, it is to be understood that the present invention is not limited to the disclosed embodiment, but may be embodied in various other forms without departing from the spirit and the scope of the present invention as defined by the appended claims.

What is claimed is:

1. A light source apparatus including a discharge lamp, said discharge lamp being subject to progressive degradation during use so that its output light intensity achievable with a given level of electrical input gradually decreases through its lifetime, said apparatus comprising:

an output light intensity control for controlling electrical input to said discharge lamp in order to maintain output light intensity of said discharge lamp at a substantially fixed, desired intensity level;

a detector for detecting an electrical parameter relating to electrical input to said discharge lamp, said electrical parameter having a tendency that its level for achieving a given level of output light intensity of said discharge lamp gradually and monotonically varies through the lifetime of said discharge lamp; and an indicator for determining when a level of said electrical parameter detected by said detector has reached a threshold level and providing an indication of necessity of discharge lamp replacement when said indicator determines so.

2. The light source apparatus according to claim 1, wherein:

said electrical parameter is input power supplied to said discharge lamp, which has a tendency that its level for achieving a given level of output light intensity of said discharge lamp gradually increases through the lifetime of said discharge lamp; and said indicator determines when a level of said input power has increased to reach a threshold power level and provides an indication of necessity of discharge lamp replacement when said indicator determines so.

3. The light source apparatus according to claim 1, wherein:

said electrical parameter is input voltage applied across said discharge lamp, which has a tendency that its level for achieving a given level of out put light intensity of said discharge lamp gradually increases through the lifetime of said discharge lamp; and said indicator determines when level of said input voltage has increased to reach a threshold voltage level and provides an indication of necessity of discharge lamp replacement when said indicator determines so.

4. The light source apparatus according to claim 1, wherein:

said electrical parameter is input current supplied to said discharge lamp, which has a tendency that its level for achieving a given level of output light intensity of said discharge lamp gradually increases through the lifetime of said discharge lamp; and said indicator determines when a level of said input current has increased to reached a threshold current level and provides an indication of necessity of discharge lamp replacement when said indicator determines so.

5. A light source apparatus according to claim 4, wherein:

said discharge lamp has a lower-limit input-current level such that said discharge lamp is incapable of stable operation unless it is supplied with input current at a level higher than said lower-limit input-current level; and said desired intensity level of output light of said discharge lamp is selected such that said discharge lamp will produce output light at said desired intensity level when it is supplied with input current at a level substantially equal to and slightly higher than said lower-limit input-current.

6. A light source apparatus according to claim 4, wherein:

said discharge lamp has a rated power designated by a manufacturer thereof; and said threshold current level is selected to be substantially equal to such a level of input current to said discharge lamp that will occur when said discharge lamp is supplied with said rated power.

7. A light source apparatus according to claim 1, wherein:

said apparatus is incorporated in a video endoscope system including an endoscope having a viewing head and a solid-state image sensor housed in said viewing head; and said apparatus provides illumination to a scene to be imaged by said solid-state image sensor.

8. A light source apparatus according to claim 7, wherein:

said video endoscope system includes a monitor having a screen for displaying thereon a scene imaged by said solid-state image sensor; and said indicator provides a visual alarm indication displayed on said screen of said monitor, indicating necessity for replacement of discharge lamp.

9. A light source apparatus including a discharge lamp, said discharge lamp being subject to progressive degradation during use so that its output light intensity achievable with a given level of electrical input gradually decreases through its lifetime, said apparatus comprising:

an output light intensity control for controlling electrical input to said discharge lamp in order to maintain output light intensity of said discharge lamp at a substantially fixed, desired intensity level, said output light intensity control comprising:

a) an output light intensity detector for detecting output light intensity of said discharge lamp and providing an intensity detection signal indicative of a detected level of output light intensity of said discharge lamp;

b) a reference signal generator for generating a reference signal indicative of a reference level corresponding to said desired intensity level of output light of said discharge lamp;

c) a differential generator connected to receive said intensity detection signal and said reference signal so as to produce an output signal indicative of a difference in level between said detection signal and said reference signal;

d) a control signal generator for responding to said output signal from said differential generator by generating a control signal; and e) a current control element for controlling input current to said discharge lamp in response to said control signal;

a detector for detecting an electrical parameter relating to electrical input to said discharge lamp, said electrical parameter having a tendency that its level for achieving a given level of output light intensity of said discharge lamp gradually and monotonically varies through the lifetime of said discharge lamp; and an indicator for determining when a level of said electrical parameter detected by said detector has reached a threshold level and providing an indication when said indicator determines so.

10. A light source apparatus including a discharge lamp, said discharge lamp being subject to progressive degradation during use so that its output light intensity achievable with a given level of electrical input gradually decreases through its lifetime, said apparatus comprising:

an output light intensity control for controlling electrical input to said discharge lamp in order to maintain output light intensity of said discharge lamp at a substantially fixed, desired intensity level;

a detector for detecting an electrical parameter relating to electrical input to said discharge lamp, said electrical parameter having a tendency that its level for achieving a given level of output light intensity of said discharge lamp gradually and monotonically varies through the lifetime of said discharge lamp, wherein said detector provides a detection signal indicative of a detected level of said electrical parameter; and an indicator for determining when the level of said electrical parameter detected by said detector has reached a threshold level and providing an indication when said indicator determines so, said indicator comprising:

a threshold signal generator for generating a threshold signal indicative of said threshold level;

a comparator connected to receive said detection signal and said threshold signal so as to produce an output signal indicative of comparison between said detection signal and said threshold signal; and an alarm generator for responding to said output signal from said comparator by selectively generating an alarm indication.

11. A light source apparatus according to claim 10, wherein:

said alarm indication comprises an indication indicating necessity for replacement of discharge lamp.

12. A light source apparatus according to claim 11, wherein:

said apparatus further comprises a monitor having a display screen; and said alarm indication comprises a visual alarm indication displayed on said screen of said monitor.

13. A light source apparatus for a video endoscope system including an endoscope with an image sensor for sensing an image under illumination provided by said light source apparatus, said light source apparatus comprising:

a discharge lamp;

a power supply for said discharge lamp;

an output light intensity detector for detecting an intensity level of output light of said discharge lamp to be supplied to said endoscope;

an electrical input control for controlling electrical input to said discharge lamp in order to maintain output light intensity of said discharge lamp as detected by said output light intensity detector at a substantially fixed, desired intensity level;

an electrical input detector for detecting electrical input to said discharge lamp; and an indicator for determining when a level of electrical input to said lamp, as detected by said electrical input detector, has reached a threshold level and providing an indication when said indicator determines so; and said desired intensity level being selected such that said discharge lamp will produce output light at said desired intensity level when it is supplied with electrical input at a level below a rated electrical input level of said discharge lamp.

14. The light source apparatus according to claim 13, wherein:

said threshold level is selected to be substantially equal to said rated electrical input level of said discharge lamp.

15. A light source apparatus according to claim 13, wherein:

said electrical input control comprises input current control for controlling input current to said discharge lamp.

16. A light source apparatus according to claim 15, wherein:

said discharge lamp has a lower-limit input-current level such that said discharge lamp is incapable of stable operation unless it is supplied with input current at a level higher than said lower-limit input-current level; and said desired intensity level of output light of said discharge lamp is selected such that said discharge lamp will produce output light at said desired intensity level when it is supplied with input current at a level substantially equal to and slightly higher than said lower-limit input-current.

17. The light source apparatus according to claim 13, wherein:

said electrical input detector provides a detection signal indicative of a detected level of electrical input to said discharge lamp; and said indicator comprises:

a threshold signal generator for getting a threshold signal indicative of said threshold level;

a comparator connected to receive said detection signal and said threshold signal so as to produce an output signal indicative of comparison between said detection signal and said threshold signal; and an alarm generator for responding to said output signal from said comparator by selectively generating an alarm indication.

18. A light source apparatus according to claim 17, wherein:

said alarm indication comprises an indication indicating necessity for replacement of discharge lamp.

* * * * *